United States Patent [19]

Brimhall, Jr. et al.

[11] Patent Number: 4,503,555

[45] Date of Patent: Mar. 5, 1985

[54] SEMI-AUTOMATIC OPTICAL SCANNING APPARATUS UTILIZING LINE INTEGRATION

[75] Inventors: George H. Brimhall, Jr.; Mark L. Rivers, both of Berkeley, Calif.

[73] Assignee: University of California, Berkeley, Calif.

[21] Appl. No.: 370,490

[22] Filed: Apr. 21, 1982

[51] Int. Cl.³ .......................... G06K 9/00; G06K 9/20
[52] U.S. Cl. .......................................... 382/6; 382/61; 377/10; 364/518
[58] Field of Search ...................... 382/6, 61; 364/416, 364/519, 518, 521, 497; 358/107; 377/10, 11; 356/39

[56] References Cited

U.S. PATENT DOCUMENTS

| | | | |
|---|---|---|---|
| 3,214,574 | 10/1965 | Landsman et al. | 382/6 |
| 3,366,794 | 1/1968 | Alvarez | 250/219 |
| 4,041,286 | 8/1977 | Sanford | 358/107 |
| 4,048,616 | 9/1977 | Hart et al. | 382/6 |
| 4,202,037 | 5/1980 | Glaser et al. | 364/518 |
| 4,232,970 | 11/1980 | Sawamura et al. | 382/6 |
| 4,354,114 | 10/1982 | Kanhaukhov et al. | 356/39 |

Primary Examiner—John C. Martin
Assistant Examiner—Michael D. Parker
Attorney, Agent, or Firm—Phillips, Moore, Lempio & Finley

[57] ABSTRACT

Analysis of images or specimens which exhibit visually distinguishable component areas of a plurality of different types, to determine the relative abundances, average sizes or other characteristics of such areas, is facilitated by a semi-automatic scanning system which includes an on-line data processor. The apparatus combines the superior area recognition ability of the human operator with the speed and ease of operation of fully automatic systems. A keyboard control unit has a plurality of manually operable keys any one of which may be actuated to drive the stage motor of a microscope through which the operator views the specimen and each of which generates a distinctive signal identifying a different specific type of area in the specimen. The data processor receives stage translation signals and the area classification signals and computes the desired data which may be visually displayed following a period of scanning. The system may be used in the mineralogical analysis of ore samples on an individual mineral grain basis and also for other purposes.

13 Claims, 13 Drawing Figures

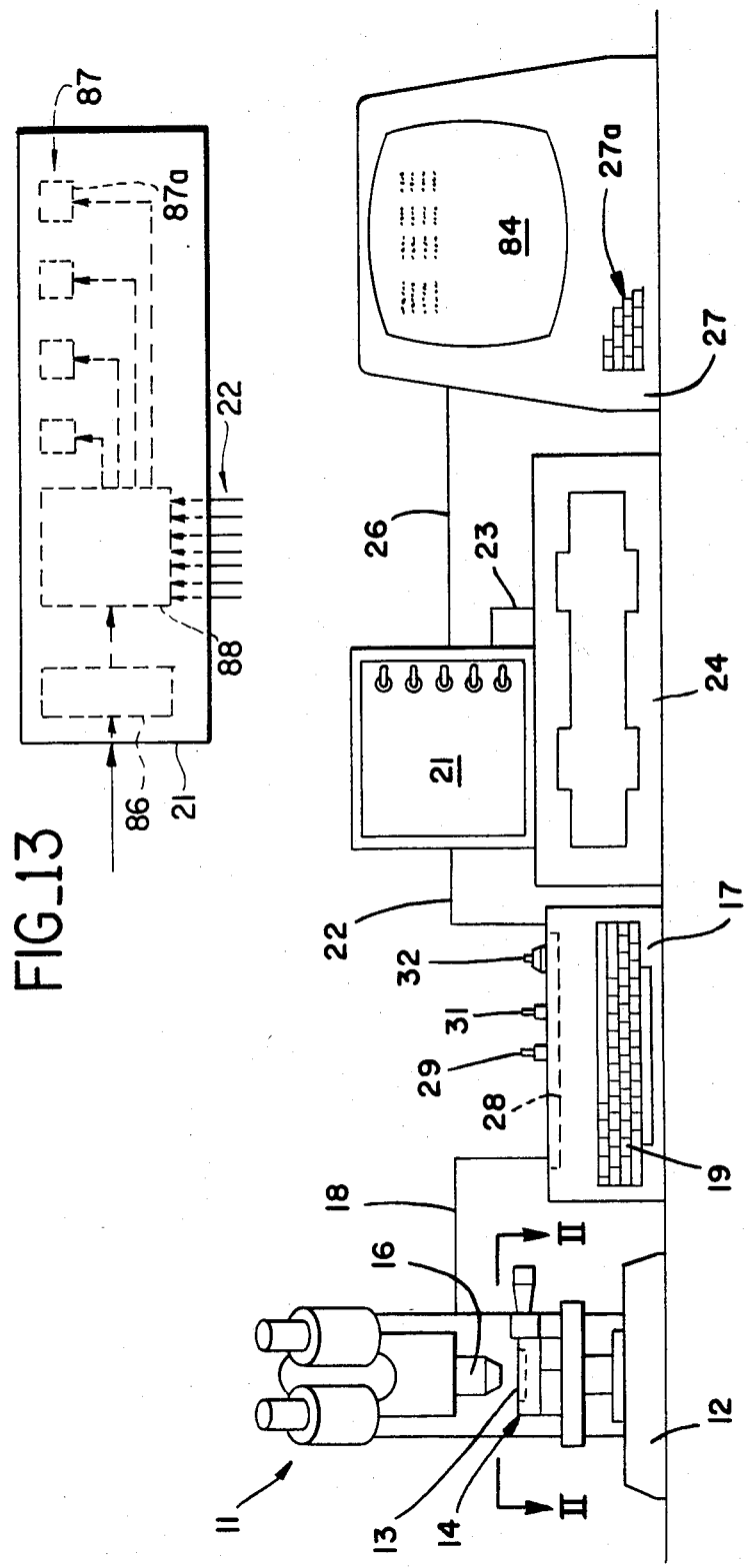

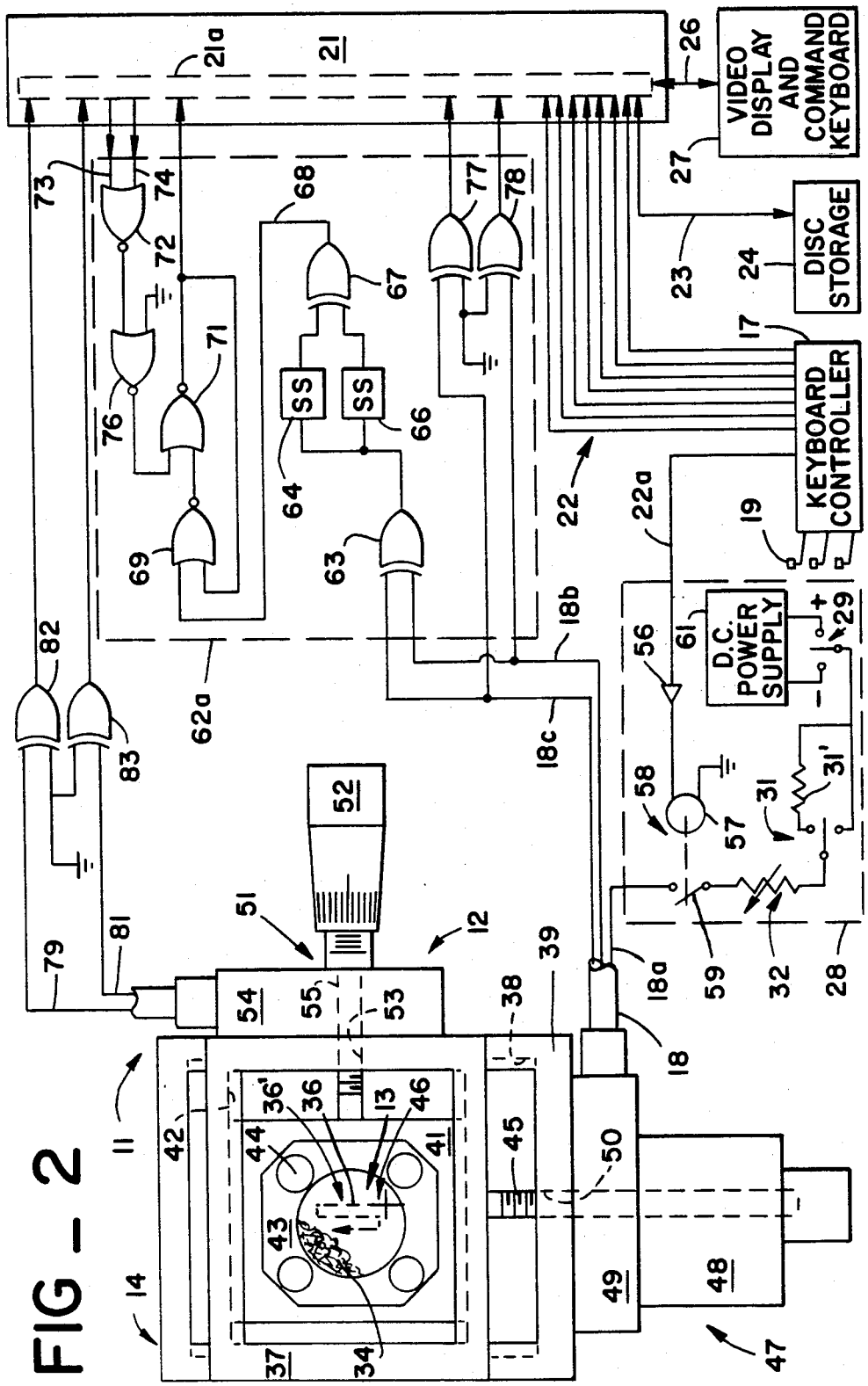

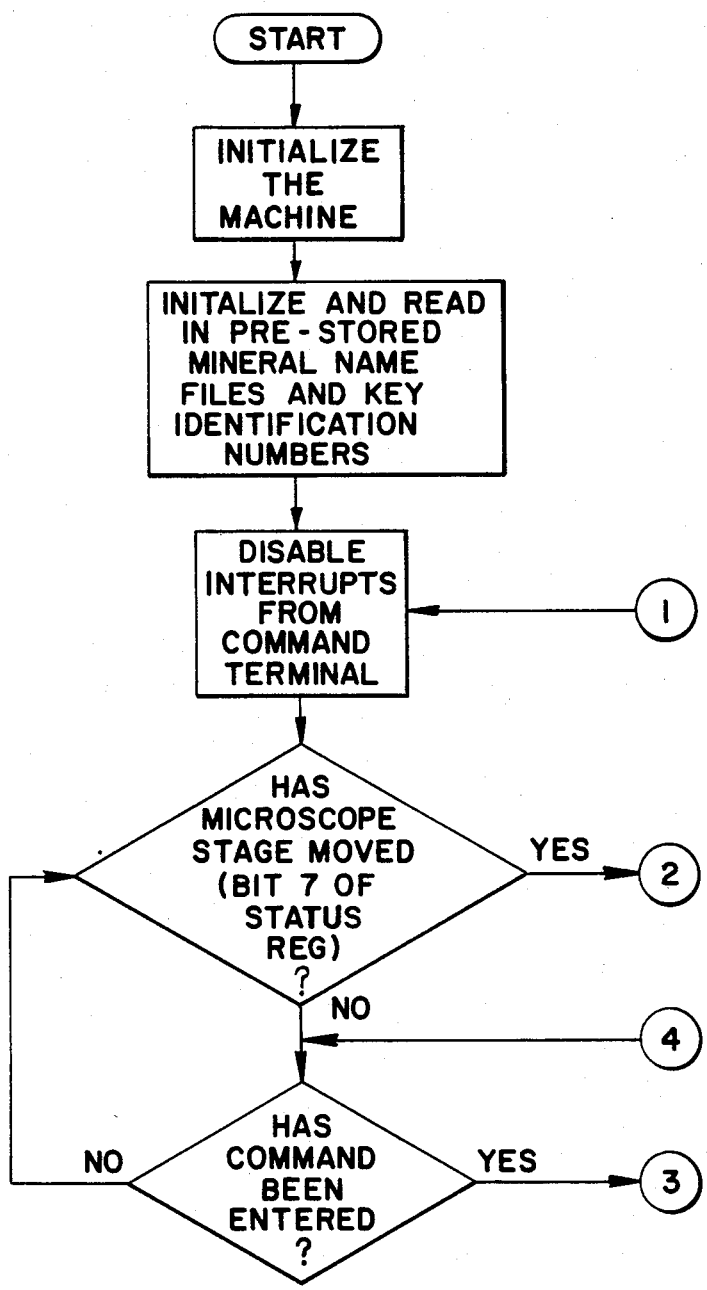
FIG _ 3

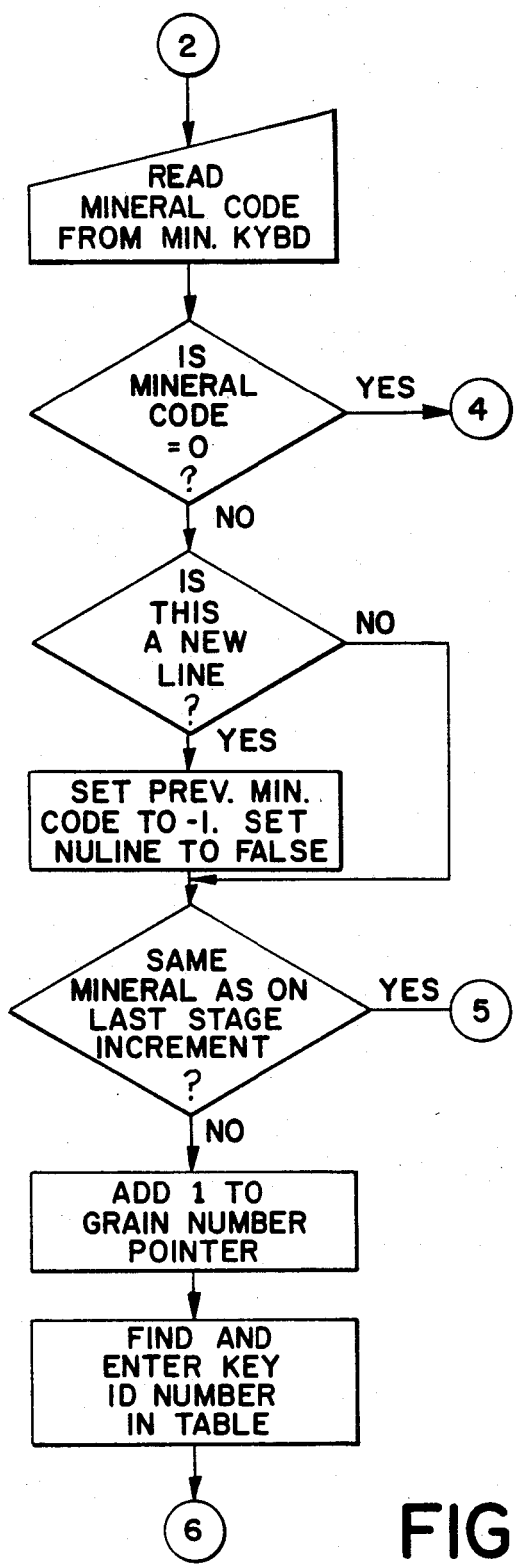
FIG_4

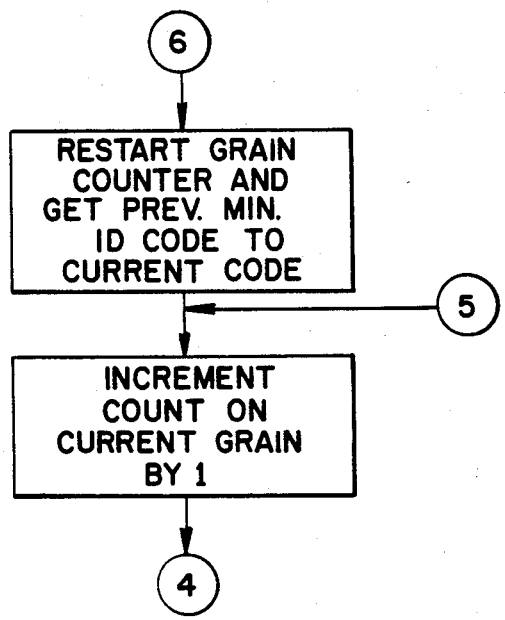
FIG _ 5
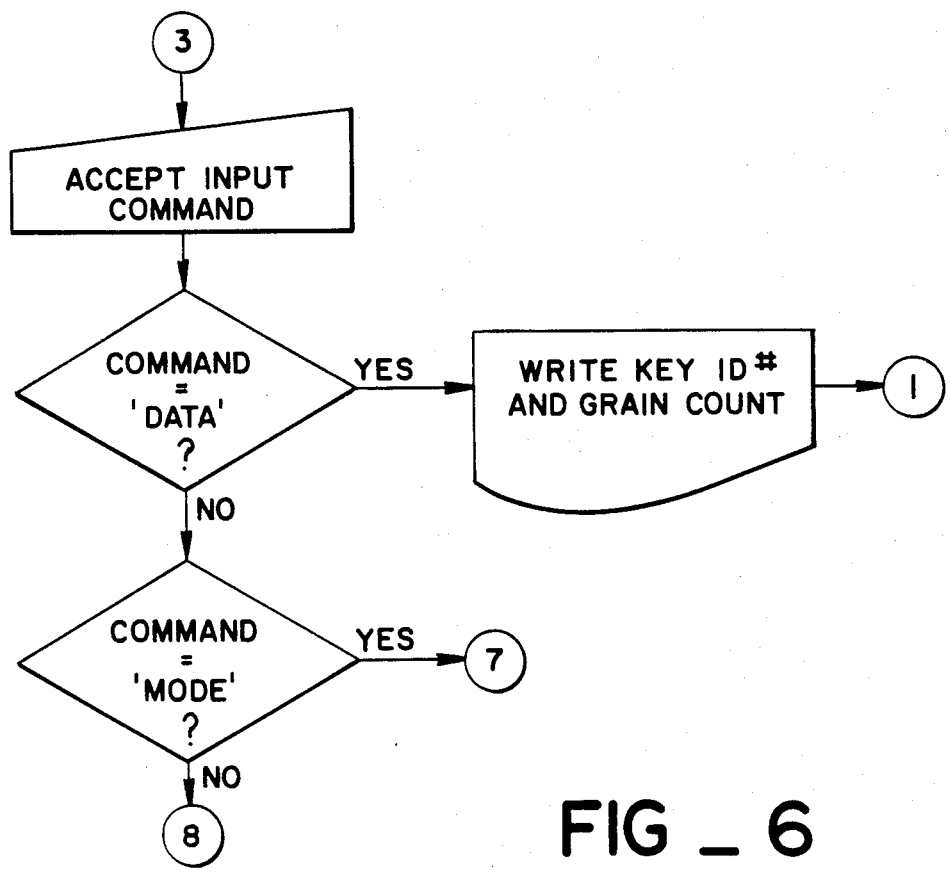
FIG _ 6

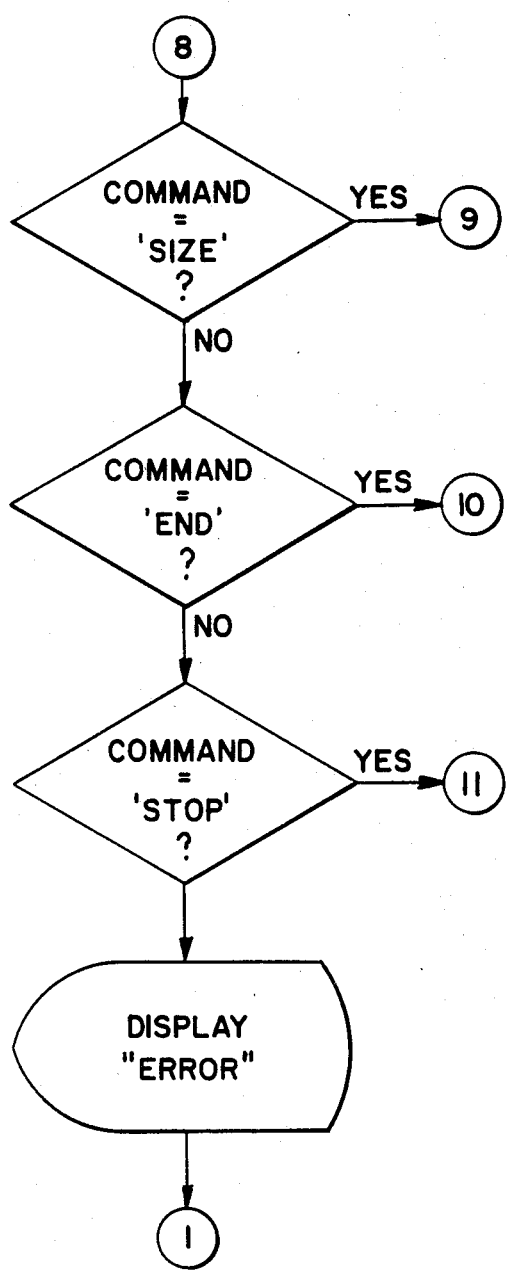
FIG _ 7

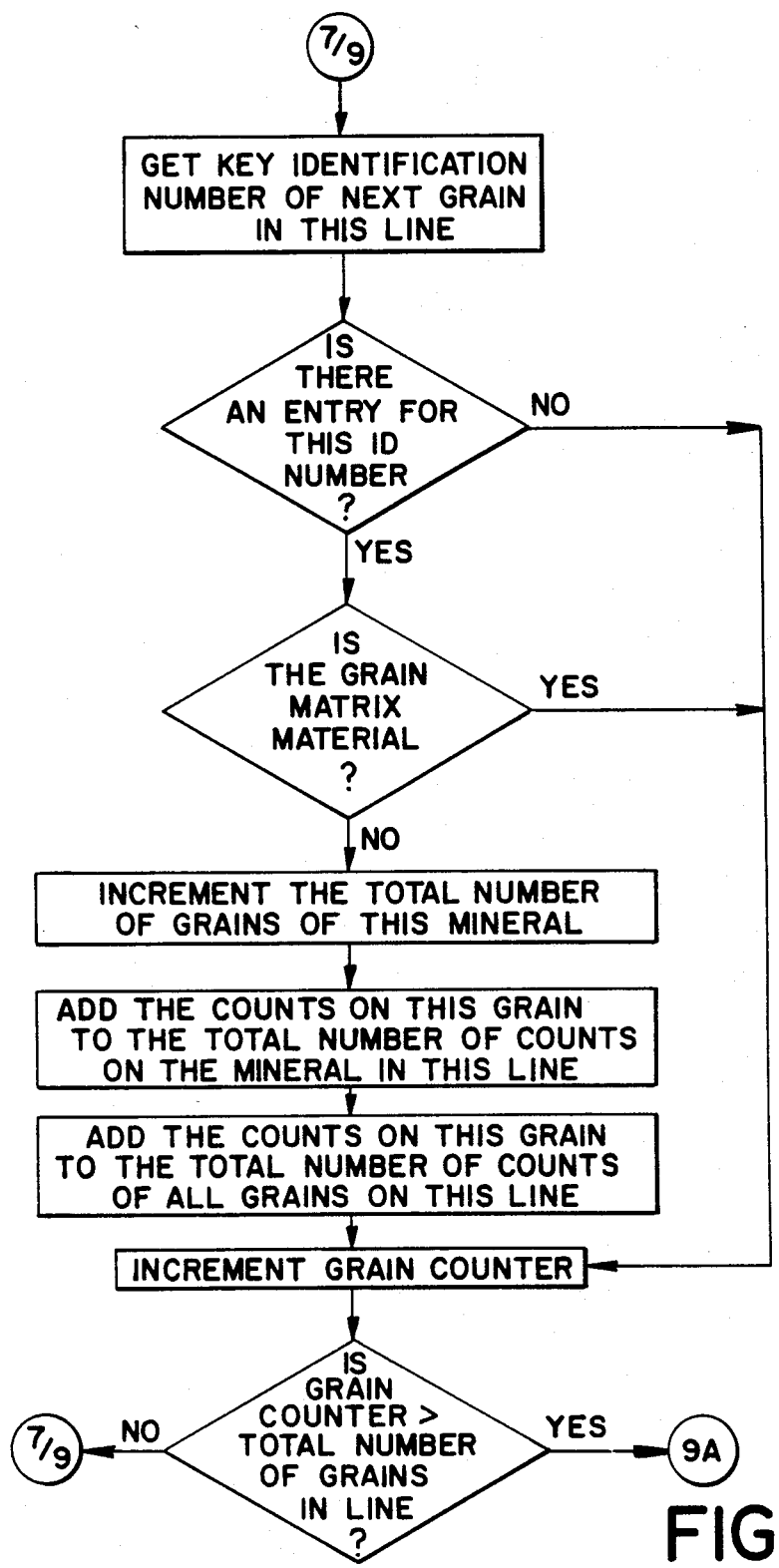
FIG_8

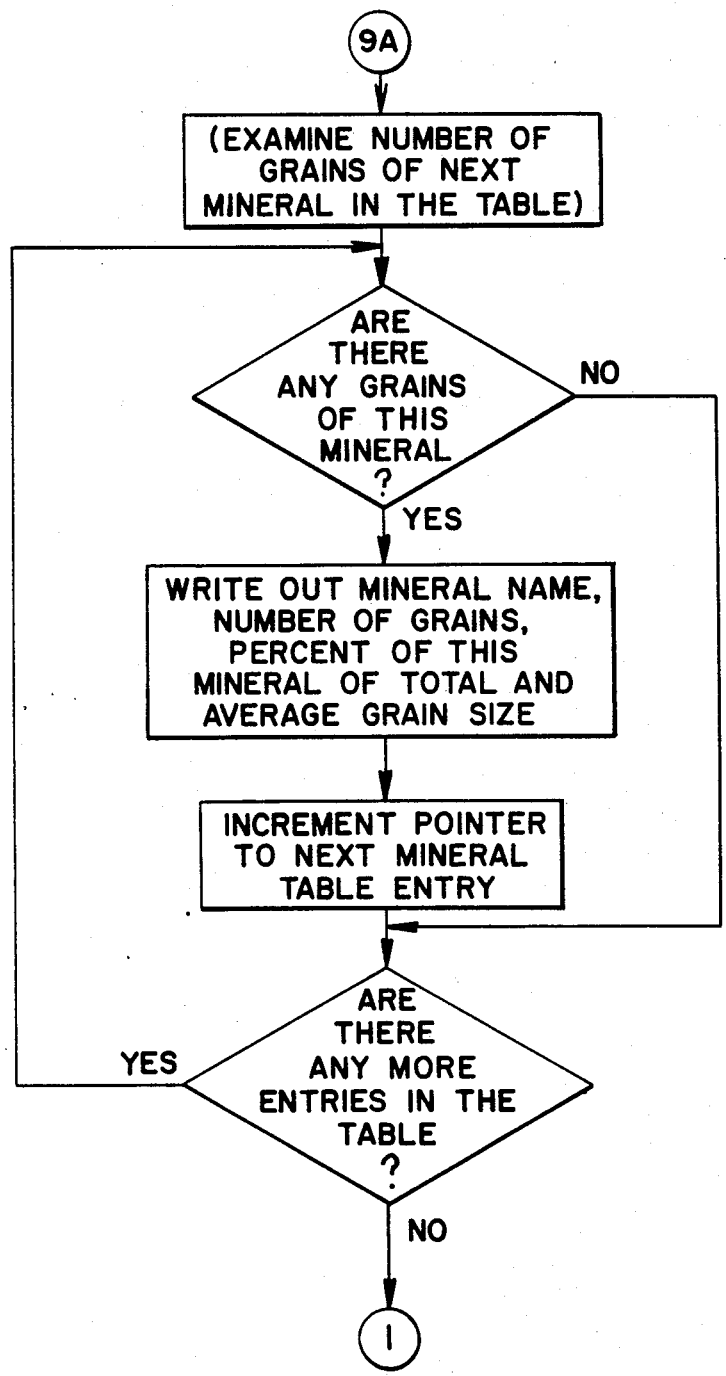
FIG_9

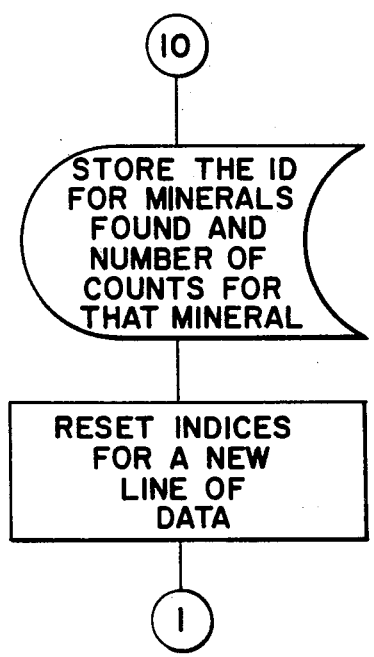
FIG _ 10
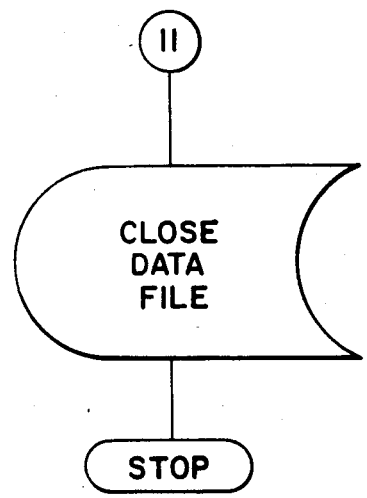
FIG _ 11

| COLUMN | | 0 | 1 | 2 | 3 | 4 | 5 | 6 | 7 |
|---|---|---|---|---|---|---|---|---|---|
| BIT PATTERN | b7 | 0 | 0 | 0 | 0 | 1 | 1 | 1 | 1 |
| | b6 | 0 | 0 | 0 | 0 | 1 | 1 | 1 | 1 |
| | b5 | 0 | 0 | 1 | 1 | 0 | 0 | 1 | 1 |
| ROW | b4 b3 b2 b1 | | 1 | 0 | 1 | 0 | 1 | 0 | 1 |
| 0 | 0 0 0 0 | 133 NUL | 1 DLE | 46 SP | 34 0 | 83 @ | 84 P | 33 ^ | p |
| 1 | 0 0 0 1 | 112 SOH | 124 DC1 | 87 ! | 37 1 | 62 A | 74 Q | 12 a | 24 q |
| 2 | 0 0 1 0 | 106 STX | 127 DC2 | 88 " | 38 2 | 56 B | 77 R | 6 b | 27 r |
| 3 | 0 0 1 1 | 104 ETX | 113 DC3 | 89 # | 39 3 | 54 C | 63 S | 4 c | 13 s |
| 4 | 0 1 0 0 | 114 EOT | 128 DC4 | 90 $ | 40 4 | 64 D | 78 T | 14 d | 28 t |
| 5 | 0 1 0 1 | 126 ENQ | 130 NAK | 91 % | 41 5 | 76 E | 80 U | 26 e | 30 u |
| 6 | 0 1 1 0 | 115 ACK | 105 SYN | 92 & | 42 6 | 65 F | 55 V | 15 f | 5 v |
| 7 | 0 1 1 1 | 116 BEL | 125 ETB | 93 ' | 43 7 | 66 G | 75 W | 16 g | 25 w |
| 8 | 1 0 0 0 | 117 BS | 103 CAN | 94 ( | 44 8 | 67 H | 53 X | 17 h | 3 x |
| 9 | 1 0 0 1 | 131 HT | 129 EM | 95 ) | 45 9 | 81 I | 79 Y | 31 i | 29 y |
| 10 | 1 0 1 0 | 118 LF | 102 SUB | 72 * | 22 : | 68 J | 52 Z | 18 j | 2 z |
| 11 | 1 0 1 1 | 119 VT | — ESC | 71 + | 21 ; | 69 K | 35 [ | 19 k | 85 { |
| 12 | 1 1 0 0 | 120 FF | — FS | 9 , | 59 < | 70 L | 49 \ | 20 l | 99 \| |
| 13 | 1 1 0 1 | 108 CR | — GS | 47 - | 97 = | 58 M | 36 ] | 8 m | 86 } |
| 14 | 1 1 1 0 | 107 SO | — RS | 10 . | 60 > | 57 N | 48 ^ | 7 n | 98 ~ |
| 15 | 1 1 1 1 | 132 SI | — US | 11 / | 61 ? | 82 O | 23 _ | 32 o | DEL |

FIG _ 12

SEMI-AUTOMATIC OPTICAL SCANNING APPARATUS UTILIZING LINE INTEGRATION

The government has rights in this invention pursuant to Grant No. EAR7911342 awarded by the National Science Foundation.

DESCRIPTION

Technical Field

This invention relates to the optical analysis of specimens or images having areas of a plurality of visually distinguishable types and to the generation of statistical data indicative of characteristics of the areas such as relative abundance or average size, for example.

BACKGROUND OF THE INVENTION

This invention was initially developed for the purpose of analyzing specimens of rock or ore to determine the abundance in the specimen of different specific mineral grains. For clarity of description the invention will be discussed with reference to that particular usage. It should be recognized that the invention is adaptable to other usages in which specimens, samples, or images are to be optically scanned in a systematic manner to identify visually distinct components while generating and processing data indicative of characteristics of one or more such components.

Statistical sampling techniques are often employed in optical scanning operations of the above described kind, particularly where the component areas to be identified and analyzed may be numerous and of small size. Prior systems for conducting this kind of analysis are either manually operated or are essentially automatic in that the operator does not perform such functions as area recognition, scan movement control and data readout and reduction.

Fully automated image analysis systems are usually based on photometric recognition of objects at a plurality of discrete sampling points in the specimen or image or on automatic areal image analysis. These automated optical scanning systems are not well suited to many specific usages including, for example, the mineralogical analysis of complex rock or ore specimens. The ability of automated systems to distinguish and identify certain types of objects, such as mineral grains for example, is at best very limited in relation to that of a human operator.

Certain of the disadvantages of automated scanning systems can be avoided by using manually operated scanning apparatus. Ore specimens, for example, can be scanned by human operators with the aid of a microscope equipped with a stage that is translatable by manual turning of any selected one of a plurality of micrometers. The operator optically scans the specimen along a series of parallel scan lines by turning selected micrometers to produce the scanning motion. The particular micrometer which is used to produce the scanning motion at any given time is dependent on the type of area being scanned at that moment, each of the micrometers being indicative of a different type of component of the image. Thus readings of the several micrometers following scanning of a given line indicates the abundance of the component identified by each micrometer along the scanned line. The micrometer readings may also be manually recorded at transition points in the course of scanning to enable computation of the average size of different mineral grains or the like.

Manual optical scanners of this kind can be more accurate than some of the automatic systems discussed above. This is in part a result of the line integration statistical sampling technique which is inherent in the manual apparatus. Continuous scanning along a line is analagous to making a nearly infinite number of point counts. The manual system also benefits from the superior ability of a human operator to distinguish and identify different components in the specimen or image.

Unfortunately, operation and reading of the micrometers is very time consuming and prone to error. There is also a practical limit on the number of micrometers which can be attached to the translation stage of the microscope thereby making it difficult at best to analyze specimens having a greater number of different areas to be identified and measured. Reduction of the readings taken from the micrometers to obtain the desired information, such as the abundance of various components of the image, may also require at least some time consuming manual arithmetical operations.

Thus fully automated optical scanning systems are subject to object recognition problems when employed for certain purposes. Manual scanning systems are very slow in operation, taxing to operate and error prone and are not well suited for analysis of specimens or images having a large number of different components to be identified.

The present invention is directed to overcoming one or more of the problems set forth above.

SUMMARY OF THE INVENTION

In one aspect of the present invention optical scanning apparatus for scanning specimens which exhibit areas of a plurality of visually distinguishable types has a visible indicia which is superimposed on the specimen as viewed by an operator, motor driven translation means for producing relative movement of the indicia and the specimen along a scan path and translation signal generating means producing signals indicative of the movement. The apparatus further includes manually actuated control means for generating any selected one of a plurality of area classification signals and a data processor coupled to the translation signal means and the manually actuated control means, the data processor including means for receiving and correlating the area classification signals and translation signals.

In another aspect, the invention includes motor control means for actuating the motor driven translation means in response to generation of any of the area classification signals at the manually actuated control means.

In still another aspect, the invention includes means for computing and indicating values corresponding to the amount of the translation movement which has occured in conjunction with at least one of the area classification signals.

In one specific aspect, the invention includes a microscope with a motor driven translatable stage and an encoder which generates counts indicative of successive increments of stage movement, the manually actuated control means being a keyboard controller having a plurality of keys any of which may be manually operated to energize the motor while causing generation of an area classification signal which identifies the particular key which is operated at any given time.

The operator maintains the motorized scanning movement by actuating different ones of the plurality of keys or the like at different times depending on the type of area which is being scanned at the particular time. As the apparatus relies on the superior area recognition capabilities of a human operator, the system provides highly accurate and reliable output data. The data is produced quickly, without time consuming and taxing procedures on the part of the operator and, in the preferred forms of the invention, is processed by an on-line computer and visually displayed. The computer may variously be programmed to determine the number and size of each distinct area in the specimen, the relative proportions of different types of area, the average sizes of each different type of area or other statistical information which may be derivable from the scanning operation.

BRIEF DESCRIPTION OF THE DRAWINGS

FIG. 1 is a front elevation view of a semiautomatic optical scanning system in accordance with one embodiment of the present invention, FIG. 2 is in part a plan view of a portion of the apparatus of FIG. 1 taken along line II—II thereof and in part a schematic electrical circuit diagram of certain control components of the apparatus depicted in the preceding figure.

FIGS. 3 to 11 are computer program flow charts.

FIG. 12 is a character chart illustrating correspondence between a keyboard which generates standard ASCII binary signals and non-ASCII key identofication numbers as used in the computer program of one embodiment of the invention.

FIG. 13 schematically depicts certain data processing means which are established within a computer by a program to be hereinafter set forth.

DETAILED DESCRIPTION OF AN EMBODIMENT OF THE INVENTION

Referring initially to FIG. 1 of the drawings, the optical scanning apparatus 11 of this particular embodiment includes a microscope 12 as a means for viewing specimens or images although other viewing arrangements are possible such as projection of images of the specimen 13 to be scanned on a screen. The microscope 12 of this example is of the known type having a motor driven translatable stage 14 for supporting the specimen 13 and for translating the specimen relative to the objective lens 16 of the microscope, the stage being hereinafter discussed in more detail.

Scanning movement at the microscope 12 is initiated and controlled by manually actuatable control means 17 which in this example is a keyboard controller coupled to the microscope through a multiconductor electrical cable 18. Keyboard controller 17 may be of the known form having an array of keys 19 for initiating digital signals each indicative of a different alphanumeric character or operation to be performed, and will also hereinafter be discussed in more detail.

Keyboard controller 17 is also coupled to a data processor or computer 21 through an additional multiconductor cable 22. Another multiconductor cable 23 links the computer 21 to an auxiliary data storage 24 which in this example is of the floppy disk type and still another cable 26 couples the computer to an input/output device 27 which includes a video display tube 84 and a command keyboard 27a in this example.

Considered separately each of the above described components of the optical scanning apparatus 11 may be of known constructions except that a microscope stage motor control circuit 28 including motor control switches 29, 31 and 32 to be hereinafter described in more detail has for convenience been mounted on the keyboard controller 17.

While other comparable components may be used, the microscope 11 of this particular example is a Universal model manufactured by the Zeiss Company of West Germany. Keyboard controller 17 in this example is model number B70-05AB manufactured by Cherry Electrical Products Corporation. Computer 21 of this example is an LSI-11/2 model as manufactured by Digital Equipment Corporation. Auxiliary data storage 24 of this example is a dual floppy disk drive, model DSD 440 manufactured by Data Systems Design. I/O device 27 of this example is a video display, model number TVI-920B manufactured by Televideo Corporation.

A variety of different specimens or subjects 13 may be scanned and analyzed by the optical scanning apparatus 11 but are, in general, subjects which exhibit visually distinguishable component areas of more than one type and in connection with which it is desired to identify the component areas and to obtain statistical data on characteristics of the different areas. The relative amounts of the different types of areas in the specimen or the average sizes of each type of area are examples of the kind of data which it may be desirable to obtain.

Considering one specific example, with reference now to FIG. 2, the specimen 13 may be a sample of rock or ore composed of many individual grains 34 of a number of different specific minerals. For clarity of illustration the individual grains 34 are depicted in FIG. 2 as being of much larger size than is typically the case. In practice the present example of the invention was designed to resolve and analyze grains 34 having sizes ranging down to one micron. The specimen 13 may be essentially natural rock specimens composed solely of juxtaposed areas 34 of different types of mineral or the specimen may be a processed one prepared from pulverized rock in which the individual component 34 grains are situated in an artificial matrix material such as epoxy plastic for example. In either case derivation of the desired data involves visual scanning by the operator along one or more linear scan paths 36 within the specimen 13 to identify individual grains 34 and recording of the types of grains 34 which are encountered and recording of the amount of scanning motion which occurs in conjunction with each different type of grain 34 that is to be analyzed.

The translatable stage 14 has a first rectangular frame 37 which is movable along ways 38 in an underlying rectangular base frame 39 to provide for movement of the specimen 13 in what will hereinafter be termed the Y-coordinate direction. A second rectangular frame 41 is carried by the first frame 37 and is slidable along ways 42 of frame 37 in an orthogonal direction, hereafter termed the X-coordinate direction. An annular specimen holder 43 in which the specimen 13 is supported may be attached to the plate 31 by disengagable means such as thumbscrews 44.

The microscope 12 superimposes a visible indicia or reference mark in the form of a cross hair 46 on the specimen 13 as viewed by the operator. Relative movement between the specimen 13 and the cross hair 46 in the Y-coordinate direction, which is the direction of the scan paths 36 in this example, is provided for by a motor driven translating mechanism 47. Translating mechanism 47 may be of the known form having an electrical drive motor 48 which turns a threaded lead screw 45 engaged in a threaded opening 50 in first frame 37 and which is coupled to the second frame 41. Mechanism 47 further includes an optical encoder 49 of the known type that generates electrical translation signals indicative of successive increments of stage movement in the Y-coordinate direction.

Suitable detailed constructions for microscope stage assemblies 14 and translation mechanisms 47 of this kind including a drive motor 48 and encoder 49 are known to the art and accordingly need not be further described. The translatable stage assembly 14 of this particular example, including frames 37, 38 and 41 is an XY mount model MR80-25 translation stage as manufactured by the Klinger Scientific Corp. although other known stage constructions may also be used. The unitized drive motor 48 and encoder 49 assembly of this example is a model BMLD 25-25 also manufactured by the Klinger Scientific Corp.

In instances where specimens 13 are to be examined only along a single linear scan path 36, translation of the specimen in the X-coordinate direction may not necessarily be required. More typically it is desired to perform a series of scans through the specimen 13 along a plurality of parallel scan lines 36. This is accomplished by shifting the specimen 13 in the X-coordinate direction following completion of scanning along each line 36 other than the final one. In this example, stage movement in the X-coordinate direction is performed manually rather than with motorized stage drive means. In particular an X-coordinate stage translation mechanism 51 is secured to first frame 37 and includes a micrometer 52 for turning a lead screw 55 that is engaged in a threaded opening 53 in frame 37 and which is coupled to the second frame 41. Thus manual turning of micrometer 52 moves frame 41 and the specimen 13 in a direction orthogonal to the movement provided by the Y-coordinate stage translation mechanism 47. The X-coordinate stage translation mechanism 51 also includes another optical encoder 54 which generates electrical signals indicative of successive increments of movement of the specimen 13 in the X-coordinate direction. The X-coordinate translation mechanism including micrometer 52 and encoder 54 may also be of a known construction and in this example is a model BMLD 25-25 cc manufactured by the Klinger Scientific Corp.

The Y-coordinate stage translation motor 48 is actuated to cause scanning movement along scan path 36 in response to the operator's depression of any selected one of the keys 19 of keyboard controller 17. The keys 19 of a standard keyboard controller 17 are each marked with a different alphanumeric character or control function symbol and operation of any of the keys generates a digitized seven bit binary signal on seven output lines 22 that identifies the particular key which is operated at any given time in standard ASCII code notation. An additional signal bit on an additional "key depressed" output line 22a is generated in response to actuation of any of the keys 19. In the context of the present invention, each of the keys 19 and the distinctive output signal produced by operation of each key is used to represent a different one of the types of areas 34, such as grains of different types of mineral, that may be present in the specimen 13. Thus the ASCII code binary signals produced by the controller 17 are, for the purposes of the present invention, area 34 classification signals and controller 17 is a manually actuatable means for generating any selected one of such signals.

The operator begins scanning of a line 36 by depressing the particular key 19 which represents the particular type of mineral grain 34 that appears under the cross hair 46 at that time. When the end of that grain is reached, that key 19 is released and the appropriate different key is then depressed to continue the scanning unless the next grain is one of the same type.

The key depressed signal or bit on keyboard controller output line 22a causes actuation of the Y-coordinate stage translation motor 48 when any of the keys 19 are operated. Motor 48 is of the reversible type in which motor operation occurs in one direction in response to a positive voltage and in the opposite direction in response to negative voltage and in which the speed of motor operation may be regulated by varying the magnitude of the applied voltage. A motor control circuit 28 is connected between the key depressed key signal output line 22a of controller 17 and the power lead 18a of motor 48. Motor control circuit 28 includes an amplifier 56 having an input connected to the key depressed signal output line 22a of controller 17 and which responds to the presence of a key depressed signal bit by energizing driver coil 57 of a relay 58. Energization of driver coil 57 closes normally open relay contacts 59 to connect motor power lead 18a with a bipolar D.C. power supply 61 through a speed control 32, high-low speed range selector 31 and forward-reverse switch 29. The forward-reverse switch 29 may be operated between two positions to selectively apply either positive or negative voltage from supply 61 to high-low speed range selector switch 32. The high-low speed switch 32 may be switched between a high speed range position at which voltage is received directly from supply 61 and an alternate low speed range position at which the voltage is received through a voltage reducing resistor 31'. From speed range selector 31, the voltage is transmitted to speed control 32 which is a manually adjustable variable resistance 32'.

Thus when the operator actuates any of the keys 19 of controller 17, relay 58 closes to energize the motor 48, the direction of motor operation being determined by the setting of forward-reverse switch 29 and the general speed range being determined by the setting of speed range selector 31. Precise variations of speed within the selected range may be made manually by adjustment of variable-resistance 32'.

To enable the computer 21 to receive, correlate, store and process the raw data generated by scanning operations at microscope 12, the output lines 22 and 22a of keyboard controller 17 are coupled to the computer 21 interface 21a. Computer interface 21a also receives pulses indicative of successive increments of Y-coordinate stage movement through a count processing circuit 62a connected between the computer interface 21a and encoder 49 of the Y-coordinate stage translating mechanism 47.

An encoder 49 of the above described type has two signal output lines 18b and 18c which alternately change electrical state as the stage drive motor 48 turns. In other words, when line 18b changes state at a particular point in the travel of stage 14 line 18c does not do so. After the next increment of travel, line 18c changes state but line 18b does not. The conditions of the two lines 18b and 18c as stage motion progresses may be represented in binary notation as: 00-10-11-01-00 . . . which sequence is continually repeated. Thus the two lines 18b and 18c alternate between being in the same state and being in opposite states as stage motion progresses. As is understood in the art, the double output channel provided by lines 18b and 18c enable the detection of a reversal of direction of the movement when that is necessary. Count processing circuit 62a of the present system functions in part to convert such signals from lines 18b and 18c into sequences of counts or pulses each indicative of successive predetermined increments of stage motion in the Y-coordinate direction and to deliver such pulses to the computer interface 21a.

Within the count processing circuit 62a, the encoder output signal lines 18b and 18c connect with seperate inputs of an exclusive OR gate 63. Two one shots or monostable multivibrator circuits 64 and 66 have inputs connected to the output of exclusive OR gate 63 with the output of each one shot being connected to separate inputs of another exclusive OR gate 67. One of the one shots 64 is of the form triggered by a high to low signal transition at the input while the other one shot 66 is triggered by a low to high transition.

As the output of exclusive OR gate 63 changes state whenever either of the encoder signal lines 18b or 18c changes state one of the one shots 64 or 66 produces an output pulse in response to each such change of state and each such pulse causes the output 68 of OR gate 67 to switch from a low condition to high condition for the duration of the pulse. Thus the output of OR gate 67 alternates between a high or binary one and a low or binary zero condition as motor 48 turns to produce the scanning movement in the Y-coordinate direction. In this example an output pulse or stage translation count is generated at gate 67 output line 68 for each micron of stage translation movement although the above described components may be selected to count other increments of motion as may be appropriate for other scanning operations.

The counts or pulses on line 68 are transmitted to one input of a two input NOR gate 69. Gate 69 has an output coupled to one input of another two input NOR gate 71 which delivers the counts to the computer interface 21a. The NOR gates 69 and 71 are provided between line 68 and the computer interface 21a to enable the computer 21 itself to terminate a count signal when it is received and being processed and also to avoid a false count which can otherwise occur when the system is first turned on. The gates 69 and 71 jointly function as a flip-flop which is set by a count signal on line 68 and which can be reset by signals from the computer. For this purpose an additional nonexclusive NOR gate has two inputs 73 and 74 from the computer interface 21a. As will be described in more detail, a high condition on either input 73 or 74 disables gate 71 to suppress transmission of counts to the computer. The computer causes input 73 to go high momentarily when a count has been received and been processed and causes input 74 to go high momentarily when the power is first turned on to suppress the false count which could otherwise be generated at that time.

The output of NOR gate 72 connects to one input of an additional NOR gate 76, the other input of gate 76 being permanently held low. The output of NOR gate 76 is connected to the remaining input of the previously described NOR gate 71 and the output of NOR gate 71 is fed back to the remaining input of the previously described NOR gate 69.

In the absence of a count suppression signal on either of input lines 73 and 74 from the computer 21, a count on line 68 causes the output of gate 69 to go low. This causes the output of gate 71 to go high thereby transmitting the count to computer interface 21a. Owing to the feedback from the output of gate 71 to one input of gate 69, the output of gate 71 remains high, after termination of the count signal on line 68, until such time as the computer returns a count suppression signal on input line 73. The count suppression signal causes the output of gate 72 to go low and that in turn causes the output of gate 76 to go high. Consequently the output of gate 71 goes low, terminating delivery of the count to computer interface 21a and resetting the count processing circuit 62a for processing of a subsequent count.

As will hereinafter be described in more detail in connection with the computer program, the computer 21 temporarily stores values corresponding to the number of stage translation counts received from circuit 62a in conjunction with each successive area classification signal from keyboard controller 17.

Thus, with reference to FIG. 13, the computer 21 is programmed to establish means 86 for counting pulses, means 87 for storing the counts of the pulses in any of a plurality of different count stores 87a and means 88 for directing counts to a different one of the count stores in response to each change of the area classification signal.

At the end of each line 36 of scanning through a specimen 13, the correlated classification signal data and count signal data for that line is transferred to auxiliary storage 24. The accumulated data for one or more lines 36 of scanning may subsequently be recalled from storage 24 for further processing by computer 21 to obtain desired information for visual presentation at display 27. The computer 21 may be programmed to compute and display the percentage of each type of area 34 in the specimen, the mean size of each type of area, the number and size of each type of area in the specimen or other desired information which is derivable from the stored data.

In the present example, scanning motion along any single scan line 36 is always in one direction and it is not necessary that the computer 21 be able to detect a reversal of such movement. In circumstances where the computer 21 may need that capability, count processing circuit 62a may include two additional exclusive OR gates 77 and 78 each of which has one input held permanently low. The other input of EX OR gate 77 is connected to encoder signal output line 18b and the other input of EX OR gate 78 is connected to encoder output signal line 18c. The outputs of gates 77 and 78 alternately change state in response to the encoder 49 output signals and undergo a phase reversal, which is detectable by computer 21, if the scanning movement reverses in the course of scanning along a scan line 36.

In many operations it is desired to scan the specimen 13 along more than one of the scan path lines 36, the successive scan lines typically being parallel. Following completion of scanning along one line 36, micrometer 53 may be manually operated to shift the specimen 13 in the X-coordinate direction a desired distance so that scanning along the next line 36 may proceed. It is less time consuming if scanning along alternate ones of the lines 36 is conducted in alternating directions as depicted by scan path 36' in FIG. 2. Reversal of the Y-coordinate stage drive motor 48 for this purpose is accomplished with the forward-reverse switch 29 of motor control circuit 28 at the completion of each individual scan line.

Scanning of the specimen 13 to identify and locate areas 34 is not necessarily conducted during the periods that the micrometer 53 is being operated to produce stage movement from one scan line to the next in the X-coordinate direction. Thus, translation signals indicative of the movement in the X-coordinate direction may not be needed in some systems including one which operates with the hereinafter described computer program. In unstances where storage of both X- and Y-coordinate data is desired, to enable subsequent relocation of specific areas 34 of the specimen for example, the X-direction translation signals may be generated by the additional encoder 54 having output signal lines 79 and 81 coupled to the computer interface 21a through additional exclusive OR gates 82 and 83 respectively. Signal line 79 connects with one input of OR gate 82 while signal line 81 connects with one input of OR gate 83, each such OR gate having the other input held permanently low and each such OR gate having an output connected to the computer interface 21a. Thus the gates 82 and 83 are essentially similar to the previously described OR gates 77 and 78 of circuit 62a and may be used in a similar manner to provide the computer 21 with counts indicative of successive increments of stage motion but in the X-direction in this case. In systems where it is desired to conduct scanning operations in the X-direction as well as in the Y-direction, the X encoder output signal lines 79 and 78 may be connected to the computer interface 21a through a separate circuit similar to the previously described count processing circuit 62a.

An example of a program for enabling the computer 21 to perform an analysis of the specimen 13 will be hereinafter presented following a description of the overall operation of the scanning apparatus 11.

OPERATION

In operation, a specimen 13 to be analyzed is mounted in the microscope 12 by attaching the specimen holder 43 to stage frame 41 with thumb screws 44. The stage 14 is then translated in the X-and Y-directions as may be necessary to bring the cross hair 46 into register with the beginning of the initial point in the scan line 36 along which scanning will proceed. Stage translation in the Y-direction is accomplished by setting forward-reverse switch 29 to the plus or minus position depending on the direction of stage movement needed to bring the cross hair 46 into register with the initial point on scan path 36'. Depending on the amount of such movement which is required high-low speed switch 31 may be operated to connect the stage translation motor 48 with forward-reverse switch 29 either directly or through the voltage dropping resistor 31' which results in a slower rate of stage translation. Adjustment of the stage 14 in the X-direction to register cross hair 46 with the scan path 36 is accomplished manually by turning micrometer 52.

The operator begins the initial line scan by identifying the particular mineral grain or area 34 which is under the cross hair 46 at that time and by then depressing the particular key 19 of controller 17 which represents that particular mineral or area. This energizes the key depressed output channel 22a of the controller 17 which in turn causes amplifier 56 to energize relay driver coil 57 and close relay contacts 59. Motor 48 then turns lead screw 49 to cause scanning movement along line 36 in the Y-direction.

When the end of the first mineral grain 34 appears under the cross hair 46, the operator releases the controller key 19 which was previously depressed, identifies the next mineral grain and depresses the controller key corresponding to the new mineral grain. This procedure is repeated each time a new mineral grain 34 is observed under the cross hair 46 in the course of the scan.

In instances where the mineral grains 34 or other areas to be analyzed are not contiguous such as where mineral grains from crushed rocks have been embedded in a plastic matrix for example, one of the keys 19 of controller 17 may be designated to represent the matrix material. Stage translation from one grain 34 to the next may then be realized by operating that particular key.

The computer 21 totalizes the counts received through gate 71 between each change in the area classification signal received from controller 17, the total number of such counts received in conjunction with each specific area classification signal being temporarily stored in the computer memory together with identification of each area classification signal.

At the end of the initial line 36 of scanning along path 36', the operator actuates a command key 27a at input-/output device 27 to cause the computer 21 to transfer the accumulated data for that line to auxiliary storage 24 where it is permanently stored on magnetic disks in this particular example although other forms of data storage may also be utilized. Operation of command key 27a also clears the accumulated data from the computer 21 itself in preparation for scanning of a subsequent line 36.

The operator then turns micrometer 52 to translate the specimen 13 a small distance in the X-direction in preparation for the subsequent line of scanning. One or more additional line scans may then be made in the same manner described above, the number of additional line scans being dependent on the degree of accuracy which is needed in the processed data.

Following a period of scanning, the operator may actuate others of the command keys 27a at I/O device 27 to obtain a readout of desired data at display screen 84. If the hereinafter described computer program is employed, there are three different types of data display available. A first type, termed the DATA display gives the raw data collected during the proceeding period of scanning in the form of an identification of each grain 34 or the like in the order in which the grains were encountered and the totalized number of stage translation counts that were received during scanning of each grain or the like. Thus the DATA display is indicative of the particular minerals which are present along the scanned region of the specimen and of the size of each such grain.

The second type of display available in this particular example of the invention is termed MODE and is a display of the percentage or relative abundance of each mineral or type of area 34 in the specimen 13. The third type of display is termed SIZE and is a readout of the mean or average size of each different mineral or type of area 34. Provided a sufficiently large sampling has been made, such data is indicative of similar characteristics of the specimen 13 as a whole.

The example of the invention herein described was designed for the mineralogical analysis of rock or ore specimens and has been described with respect to that specific usage to facilitate an understanding of basic aspects of the invention. An essentially similar system may be used for any of a variety of other geological or nongeological purposes where specimens or images exhibit component areas 34 of a variety of different types and similar statistical data on such areas is desired. An essentially similar system may, for example, be used for the analysis of vegetation zones, agricultural crops, land usage or the like in aerial photographs. A similar system may also be employed for various medical research or diagnostic purposes such as in the analysis of blood or tissue samples for example.

SOFTWARE

Considering now a suitable program for implementing the above described functions of the computer 21, reference should be made to FIGS. 3 through 11 to understand the logic utilized in the computer programs. A data file containing a representative listing of minerals expected to be found in an ore sample to be scrutinized is necessary for operation of this system. Since the generation of this table is well within the capability of most editing systems now available in small computing systems, it will be assumed that this table has been generated by the user. It should be understood that if this particular invention is utilized in an environment other than ore sample checking, that the table of variables comparable to the minerals would likewise be available at the outset of the use of the invention.

In order to better understand the software aspects of this system, it should be understood that in this particular application the input/output device 27 having a video display and a command keyboard serves the function of receiving commands from the operator while the keyboard controller 17 is used to identify the particular mineral being scanned and to cause the stage to be advanced at a particular rate. While two keyboards are utilized in this particular invention, it should be understood that with appropriate software and by utilization of one of the command key strokes on a single keyboard, a single keyboard could suffice to operate the invention.

The computer program is started by initializing and reading in the mineral names in the prestored file as indicated in FIG. 3. Once the mineral names have been read into computer 21 from disk storage 24 or some other peripheral device a wait loop is entered into by disabling interrupts from the command terminal 27. The program then checks to see if the microscope stage 41 has been moved by checking the output of controller 17 which is reflected in the output of gate 71. In the case of controller 17, an eight bit code is generated upon actuation of a key. Bits zero through six generated by controller 17 constitute the binary ASCII code of the character selected at the keyboard while bit seven is always a binary one. (See FIG. 11). As noted above this binary one is used to move the stage through the circuitry previously described. Such stage movement changes the status of gate 71 in the manner previously described and this; in turn sets bit seven of the status register of computer 21. If the microscope stage has moved, (bit seven of the status register) the program shifts to a subroutine to collect data. If on the other hand the microscope stage has not moved, the program checks for a command from input/output device 27. It should be noted that in the disabling condition set forth above, only the normal supervisory interrupts have been disabled. Nevertheless the keyboard console 27a on input/output device 27 is still operative and can generate a code. Thus the program will check and see if a code has been generated in which case the console interrupts are reenabled. More will be said about this in the discussion of the command processing mode.

If the microscope stage has moved, the program calls a subroutine to collect data. (See FIG. 4.) After initializing the data collection phase for the first time, the program will check to see if the same mineral key is depressed in which case the grain counter will be incremented. If a new mineral number has been identified, that new identification will be added to the grain number table and the grain counter will be reset to accumulate the counts for that particular new mineral grain. The program then returns to the wait loop in the initial portion of the program where it will continue to loop until a signal is either received that the microscope stage has moved again or that a command has been entered.

This process is accomplished in the described hardware and software by the operator pressing one of the keys 19 on controller 17 to cause stage 14 to move along a given axis. After stage 14 has moved one micron bit seven of the status register of computer 21 is set to one by flip/flop 69/71 which is high as a result of the stage movement. The program detects the one in bit seven of the status register in the "wait loop" and then jumps to the data collection subroutine where it reads the contents of the data register. The data register contains the mineral identification code of the particular depressed key 19. After reading the data register, the program clears flip/flop 69/71 by outputting a one on line 73 thereby readying the system for additional data collection.

If a command has been entered from the command console, (see FIG. 6) the particular command is identified and a subroutine called to perform that particular function. There are four basic commands programmed into this system, "data", "mode", "size", and "end". In addition to these four basic commands, a "stop" command is provided to cease all operations in the system. The "data" command will generate a listing of the key identification numbers and the grain counts associated with those particular key identification numbers at any time during the scan. The command "mode" and the command "size" generate the same data in this particular application although the commands can be separated to provide distinctly different data. In this particular program, the command "mode" (or "size") will generate a listing of the mineral names corresponding to the key identification numbers, the number of grains of that particular mineral, the percent of that particular mineral for a particular scan line and the mean grain size of that particular mineral. Finally the command "end" is utilized at the end of a scan line so that identification for the minerals found and the number of counts for that mineral are stored on disk storage in disk storage device 24. The "end" command also will reset all the indices for a new line of data.

It should be noted that the command phase can be entered at any time however it is inappropriate to energize a key on controller 17 and a key on input/output device 27 concurrently.

It should be understood that the wait loop found in FIG. 3 is useful in this particular application since there are two input devices which must be checked sequentially at a rather rapid rate to determine if an input has arrived from either one of the devices.

In the program listing that follows the specification at the subroutine COUNTR a data table named KEYNUM is included. This KEYNUM table is utilized as a key entry or an index entry into the mineral table. An inspection of that table in conjunction with FIG. 12 which is a code listing will show the order of the table. One will note that the space bar which is the thirty-second character in the ASCII table shown in FIG. 12 is represented in the thirty-second entry in the KEYNUM table by the number 001. Likewise the character z, which is at the lower left hand corner of any conventional keyboard and is the one hundred twenty-second character in an ASCII table, is the one hundred twenty-second entry in the KEYNUM table in the subroutine counter and carries the numeral 002. A correspondence between the particular character as represented by the key stroke in the ASCII character set is shown in FIG. 12. Thus the letter z carries with it the numeral 2 and the space bar carries the numeral 1. It should be apparent that the ordered sequence utilized in this particular program starts at the lower left hand corner of a standard keyboard and proceeds from left to right. An ordinary keyboard contains 49 or 50 keys. With the shift key, 98 to 100 unique characters are then available from the keyboard. In the particular application described herein the keyboard has a third level thus giving upwards of 150 possible characters, however the seven bit character set limits the possible characters to exactly 128. In the present application not all of the 128 characters are used.

---

PROGRAM LISTING

PROGRAM COUNT2

```
C
C       THIS PROGRAM CONTROLS THE MICROSCOPE
C       COUNTING STAGE TO DETERMINE MINERAL
C       MODES AND GRAIN SIZE DISTRIBUTIONS
C
        IMPLICIT INTEGER (A-Z)
        LOGICAL NULINE
        REAL GRCTS,COMAND
C
C
        COMMON /FILES/ LSTREC
        COMMON /NAMES/ MINAMS(140,10)
        COMMON /GRAINS/ GRNUMS(3000),GRCTS(3000),
        GNUM
        COMMON /ADDRES/ PBSTRG,PMDABU,PEDABU,
        PBVECT,
      1 CNSTRG
        COMMON /LINE/ NULINE,LINNUM
C
        DATA PBSTRG,PMDABU,PEDABU,PBVECT/"171000,
      1 "171004,"171005,"204/
        DATA CNSTRG,CNINBU,CNOUST,CNOUBU/"177560,
      1 "177562,"177564,"177566/
C
        MAXGRN=3000
C
        CALL START
C
1       TYPE 2
2       FORMAT (/' COLLECT DATA:'//)
        CALL IPOKEB(CNSTRG,0)
3       IREADY=IPEEK(PBSTRG)
        IF (IREADY.GE.0) GO TO 5
        CALL COUNTR
5       IREADY=IPEEKB(CNSTRG).AND."377
        IF (IREADY.LT."200) GO TO 3
        ID=IPEEKB(CNINBU)
        CALL IPOKEB(CNOUBU,ID)
        CALL IPOKEB (CNSTRG,"100) !ENABLE CONSOLE
      1 INTERRUPTS
        CALL CLEAR
10      TYPE 15
15      FORMAT (' ENTER COMMAND: ',$)
        ACCEPT 20, COMAND
20      FORMAT(A4)
C
        IF (COMAND.EQ.'DATA') GO TO 100
        IF (COMAND.EQ.'MODE') GO TO 200
```

---

PROGRAM LISTING -continued

```
        IF (COMAND.EQ.'SIZE') GO TO 300
        IF (COMAND.EQ.'END') GO TO 400
C
        IF (COMAND.EQ.'STOP') GO TO 1000
        TYPE 30
30      FORMAT (/' NOT A VALID COMMAND,
        TRY AGAIN.')
        GO TO 1
C
C       TYPE OUT RAW DATA
100     TYPE 110
110     FORMAT (//' RAW COUNT DATA:/,/1X,5('KEY
      1 COUNTS',4X))
        DO 150 I=1,GNUM,5
        TYPE 120, (GRNUMS(I+J),GRCTS(I+J),J=0,4)
120     FORMAT (1X,5(I3,2X,F6.0,4X))
150     CONTINUE
C
        GO TO 1
C
200     CALL COMPUT(1)
        GO TO 1
C
C
300     CALL COMPUT(2)
        GO TO 1
C
C
400     NULINE=.TRUE.
        LINNUM=LINNUM + 1
        DO 420 I=1,GNUM,40
        LSTREC=LSTREC + 1
        WRITE (1'LSTREC) LINNUM,GNUM,(GRNUMS(I+J),
      1 GRCTS(I+J),J=0,39)
420     CONTINUE
C
        DO 450 I=1,MAXGRN
        GRNUMS(I)=0
        GRCTS(I)=0
450     CONTINUE
        GNUM=0
        GO TO 1
C
1000    CLOSE(UNIT=1)
        STOP
        END
```

SUBROUTINE START

```
C
C       THIS SUBROUTINE OPENS THE FILES FOR A RUN,
        ETC. IMPLICIT INTEGER (A-Z)
C
        BYTE FILNAM(14)
        REAL GRCTS
        LOGICAL NULINE
C
        COMMON /GRAINS/ GRNUMS(3000),GRCTS(3000),
        GNUM
        COMMON /FILES/ LSTREC
        COMMON /NAMES/ MINAMS(140,10)
        COMMON /LINE/ NULINE,LINNUM

MAXGRN=3000
        CALL CLEAR
        TYPE 50
50      FORMAT(1X,T20,'COMPUTER ASSISTED MODAL
        ANALYSIS
      1 PROGRAM',
      2 /T20,'MARK L. RIVERS',
      3 /T20,'JULY, 1980',
      4 /T20,'LAST UPDATE JULY,1980')
C
        TYPE 60
60      FORMAT (//' ENTER THE NAME OF THE FILE
      1 CONTAINING YOUR MINERAL',' NAMES ETC.:')
        ACCEPT 70, FILNAM
70      FORMAT(14A1)
C
        DO 100 I=1,14
100     IF (FILNAM(I).EQ.' ') FILNAM(I)=0 ! REPLACE
C       BLANKS BY NULS
```

PROGRAM LISTING

```
C
      OPEN (UNIT=1,TYPE='OLD',NAME=FILNAM)
C
      DO 180 I=1,140
      DO 180 J=1,10
      MINAMS(I,J)=' '
180   CONTINUE
C
      DO 200 I=1,140
      READ (1,150,END=300) MINNUM,
      (MINAMS(MINNUM,J),
     1 J=1,10)
150   FORMAT(I5,10A2)
200   CONTINUE
C
300   CLOSE(UNIT=1)
      TYPE 400
400   FORMAT(' ENTER THE NAME OF THE FILE TO
      CONTAIN
     1 THE DATA YOU COLLECT.:')
      ACCEPT 70, FILNAM
C
      DO 420 I=1,14
420   IF (FILNAM(I).EQ.' ') FILNAM(I)=0
      OPEN (UNIT=1,NAME=FILNAM,TYPE='NEW',
     1 ACCESS='DIRECT',DISP='SAVE',
     2 RECORDSIZE=64,MAXREC=100)
C
C     SET ALL VARIABLES TO THEIR INITIAL VALUES
      GNUM=0
      LINNUM=0
      LSTREC=0
      NULINE=.TRUE.
      DO 500 I=1,MAXGRN
      GRNUMS(I)=0
      SUBROUTINE COMPUT(METHOD)
C
      IMPLICIT INTEGER (A-Z)
      REAL GRCTS,TOTCTS,MINCTS(140)
      DIMENSION MINGRN(140)
C
      COMMON /GRAINS/ GRNUMS(3000),GRCTS(3000),
      GNUM
      COMMON /NAMES/ MINAMS(140,10)
C     THIS SUBROUTINE COMPUTES THE MODE OF THE
C     LINE IF METHOD=1, AND THE GRAIN SIZE
C     DISTRIBUTION IF METHOD=2
C
      GO TO (200,200) METHOD
C
200   TYPE 210
210   FORMAT (//' MODAL COMPUTATION:')
      TYPE 215
215   FORMAT(/' MINERAL',T25,'VOLUME %',T40,'# OF
     1 GRAINS',T55,'MEAN GRAIN SIZE'/)
C
      TOTCTS=0
      DO 230 I=1,140
      MINCTS(I)=0
      MINGRN(I)=0
230   CONTINUE
C
      DO 240 I=1,GNUM
      NUMI=GRNUMS(I)
      IF (NUMI.EQ.1) GO TO 240 ! SKIP MATRIX
C     MATERIAL
      IF (NUMI.EQ.0) GO TO 240 ! SKIP COUNTS WHEN
C     'COASTING'
      MINGRN(NUMI)=MINGRN(NUMI) + 1
      MINCTS(NUMI)=MINCTS(NUMI) + GRCTS(I)
      TOTCTS=TOTCTS + GRCTS(I)
240   CONTINUE
C
C     TYPE OUT MODE
      DO 260 I=1,140
      IF (MINGRN(I).EQ.0) GO TO 260 ! NO GRAINS OF
     1 THIS
      TYPE 250, (MINAMS(I,J),J=1,10),MINCTS(I)/
     1 TOTCTS*100.,MINGRN(I),MINCTS(I)/MINGRN(I)
250   FORMAT(1X,10A2,T25,F10.5,T40,I5,T55,F10.3)
C
260   CONTINUE
      RETURN
      END
      SUBROUTINE COUNTR
C
C     THIS ROUTINE IS ENTERED WHEN THE STAGE
C     HAS TRANSLATED ONE INCREMENT. IT READS
C     THE MINERAL KEYBOARD TO FIND OUT WHAT
C     KEY IS PRESSED, AND INCREMENTS THE
C     COUNTS ON THE GRAIN.
      IMPLICIT INTEGER (A-Z)
C
      LOGICAL NULINE
      REAL GRCTS
C
      DIMENSION KEYNUM(128)
C
      COMMON /LINE/ NULINE
      COMMON /GRAINS/ GRNUMS(3000),GRCTS(3000),
      GNUM
      COMMON /ADDRES/PBSTRG,PMDABU,
      PEDABU,PBVECT
C
      DATA KEYNUM/
     1 112,106,104,114,126,115,116,117,131,118
     2 119,120,108,107,132,133,124,127,113,128,
     3 130,105,125,103,129,102,000,000,000,000,
     4 000,001,087,088,089,090,091,092,093,094,
     5 095,072,071,009,047,010,011,046,037,038,
     6 039,040,041,042,043,044,045,022,021,059,
     7 097,060,061,034,062,056,054,064,076,065,
     8 066,067,081,068,069,070,058,057,082,083,
     9 074,077,063,078,080,055,075,053,079,052,
     1 035,049,036,048,023,084,012,006,004,014,
     2 026,015,016,017,031,018,019,020,008,007,
     3 032,033,024,027,013,028,030,005,025,003,
     4 029,002,085,099,086,098,000,000/
C
C
C     IN COMMON BLOCK "GRAINS", GRNUMS(N) IS THE
C     KEY IDENTIFICATION NUMBER FROM ARRAY
C     KEYNUM CODE FOR GRAIN N, GRCTS(N) IS THE
C     NUMBER OF COUNTS (MICRONS) ON THAT GRAIN.
C
C
C     READ IN THE MINERAL KEYBOARD
      CMIN=IPEEKB(PMDABU).AND.=#177
      IF (CMIN.EQ.0) GO TO 2000 ! COASTING
C
C     SEE IF THIS IS THE BEGINNING OF A NEW LINE
      IF(.NOT.NULINE) GO TO 50
C
C     IT IS A NEW LINE
      PMIN=-1
      NULINE=.FALSE.
C
50    IF (CMIN.EQ.PMIN) GO TO 400
C
C     IT IS A NEW MINERAL, STORE NEW KEY NUMBER,
C     ZERO COUNTERS
      GNUM=GNUM + 1
      GRNUMS(GNUM)=KEYNUM(CMIN)! CONVERT
      FROM ASCII
     1 CODE TO MINERAL NUMBERS
      GRCTS(GNUM)=0.
      PMIN=CMIN
C
C
400   GRCTS(GNUM)=GRCTS(GNUM) + 1.
C
2000  RETURN
      END
```

While the invention has been described with respect to a specific embodiment for purposes of example, it is not intended to limit the invention except as defined in the following claims.

We claim:
1. In optical scanning apparatus for scanning specimens which exhibit areas of a plurality of visually distinguishable types, the apparatus having a visible indicia which is superimposed on the specimen as viewed by an operator, motor driven translation means for producing relative movement of said indicia and said specimen along a scan path therein, and translation signal generating means for producing translation signals each of which is indicative of a successive increment of said movement, the improvement comprising;
   manually actuated control means for generating any selected one of a plurality of area classification signals, each of said area classification signals being distinctive from the others thereof, said control means having a plurality of area classification signal initiating elements each of which may be manually actuated to cause generation of a different one of said area classification signals,
   motor control means for actuating said motor driven translation means in response to manual actuation of any of said plurality of signal initiating elements of said control means, and
   a data processor coupled to said translation signal means and said manually actualted control means, said data processor including means for registering a value indicative of the number of said translation signals that are produced during each actuation of any of said area classification signal initiating elements.

2. In optical scanning apparatus for scanning specimens which exhibit areas of a pluraltiy of visually distinguishable types, the apparatus having a visible indicia which is superimpsed on the specimen as viewed by an operator, motor driven translation means for producing relative movement of said indicia and said specimen along a scan path therein, and translation signal generating means for producing translation signals indicative of said movement, the improvement comprising:
   manually actuated control means for generating any selected one of a pluraltiy of area classification signals, each of said area classification signals being distinctive from the others thereof, and
   a data processor coupled to said translation signal means and said manually actuated control means, said data processor including means for receiving and correlating said area classification signals and said translation signals,
   wherein said data processor includes means for computing and indicating values corresponding to the amount of said movement which has occurred in conjunction with at least one of said plurality of area classification signals.

3. In optical scanning apparatus for scanning specimens which exhibit areas of a plurality of visually distinguishable types, the apparatus having a visible indicia which is superimposed on the specimen as viewed by an operator, motor driven translation means for producing relative movement of said indicia and said specimen along a said path therein, and translation signal generating means for producing translation signals indicative of said movement, the improvement comprising:
   manually actuated cotnrol means for generating any selected one of a pluraltiy of area classification signals, each of said area classification signals being distinctive from the others thereof, and
   a data processor coupled to said translation signal means and said manually actuated control means, said data processor including means for receiving and correlating said area classification signals and said translation signals,
   wherein said data processor includes means for computing and indicating values corresponding to the proportion of a predetermined amount of said movement that has occurred in conjunction with each individual one of said plurality of different area classification signals.

4. In optical scanning apparatus for scanning specimens which exhibit areas of a plurality of visually distinguishable types, the apparatus having a visible indicia which is superimposed on the specimen as viewed by an operator, motor driven translation means for producing relative movement of said indicia and said specimen along a scan path there, and translation signal generating means for producing translation signals indicative of said movement, the improvement comprising:
   manually actuated control means for generating any selected one of a plurality of area classification signals, each of said area classification signals being distinctive from the others thereof, and
   a data processor coupled to said translation signal means and said manually actuated control means, said data processor including means for receiving and correlating said area classification signals and said translation signals,
   wherein said data processor includes means for computing and indicating values corresponding to the average amount of said movement which accompanies each individual one of said area classification signals.

5. In optical scanning apparatus for scanning specimens which exhibit areas of a plurality of visually distinguishable types, the apparatus having a visible indicia which is superimposed on the specimen as viewed by an operator, motor driven translation means for producing relative movement of said indicia and said specimen along a scan path therein, and translation signal generating means for producing translation signals indicative of said movement, the improvement comprising:
   manually actuated control means for generating any selected one of a plurality of area classificaiton signals, each of said area classification signals being distinctive from the others thereof, and
   a data processor coupled to said translation signal means and said manually actuated control means, said data processor including means for receiving and correlating said area classification signals and said translation signals,
   wherein said translation signal generating means produces electrical pulses in response to successive increments of said movement and wherein said data processor includes:
   means for counting said pulses,
   means for storing totalized counts of said pulses in any of a plurality of different count stores, and
   means for directing counts to a different one of said count stores in response to each change of said area classification signal.

6. Optical scanning apparatus as set forth in claim 5 wherein said translation signal generating means includes a flip-flop having an output coupled to said data processor to transmit said counts thereto further including means for setting said flip-flop in response to said electrical pulses, and means for resetting said flip-flop in response to receipt of said counts by said data processor.

7. In optical scanning apparatus for scanning specimens which exhibit areas of a plurality of visually distinguishable types, the apparatus having a visible indicia which is superimposed on the specimen as viewed by an operator, motor driven translation means for producing relative movement of said indicia and said specimen along a scan path therein, and translation signal generating means for producing translation signals indicative of said movement, the improvement comprising:

manually actuated control means for generating any selected one of a plurality of area classification signals, each of said area classification signals being distinctive from the others thereof, and a data processor coupled to said translation signal means and said manually actuated control means, said data processor including means for receiving and correlating said area classification signals and said translation signals, wherein said data processor temporarily stores digitized values corresponding to the amount of said movement which occurs in conjunction with each of said area classification signals, further including an auxiliary data storage and means for transfering said digitized values from said data processor to said auxiliray data storage following a predetermined amount of said movement.

8. In scanning apparatus with which an operator scans specimen to detect visually distinguishable different areas thereof, the combination comprising:

viewing means for superimposing a reference mark on said specimen as viewed by said operator, translation means for producing movement of said specimen relative to said reference mark, said translation means including an electrical motor which causes said movement, encoder means for generating successive counts indicative of successive increments of said movement, a controller having a plurality of manually operable elements each of which may be selectively operated independently of the others thereof, first electrical circuit means for energizing said motor in response to operation of any selected one of said plurality of manually operable elements, second electrical circuit means for generating area classification signals which identify the particular one of said elements which is operated at any given time, and a data receiver coupled to said encoder means and to said second electrical circuit means and having means for registering said counts and for registering the area classification signals produced by said second electrical circuit means during generation of the registered counts.

9. Scanning apparatus as set forth in claim 8 wherein said viewing means is a microscope and said translation means includes a translatable stage thereof and wherein said plurality of manually operable elements are the keys of a keyboard controller which includes said second electrical circuit means.

10. Scanning apparatus as set forth in claim 8 wherein said data receiver includes data processing means for computing values corresponding to the totals of said counts which have been received in conjunction with receipt of each of said area classification signals.

11. Scanning apparatus as set forth in claim 10 further including display means for producing a visible display of said values on a screen after a selected amount of said movement.

12. Scanning apparatus as set forth in claim 9 wherein said data receiver includes data processing means for computing values corresponding to the proportion of a plurality of said counts which have been received in conjunction with each of said area classification signals.

13. Scanning apparatus as set forth in claim 8 wherein said data receiver includes data processing means for computing values corresponding to the average number of said counts which have been received in conjunction with each of said area classification signals.

* * * * *

UNITED STATES PATENT AND TRADEMARK OFFICE
CERTIFICATE OF CORRECTION

PATENT NO. : 4,503,555

DATED : March 5, 1985

INVENTOR(S) : George H. Brimhall, Jr.; Mark L. Rivers

It is certified that error appears in the above-identified patent and that said Letters Patent is hereby corrected as shown below:

Col. 17, line 32 "pluraltiy" should be --plurality-- line 34 "superimpsed" should be --superimposed-- line 41 "pluraltiy" should be --plurality-- line 60 "said" should be --scan-- line 63 "cotnrol" should be --control-- line 64 "pluraltiy" should be --plurality--

Signed and Sealed this

Eighteenth Day of June 1985

[SEAL]

Attest:

DONALD J. QUIGG

Attesting Officer      Acting Commissioner of Patents and Trademarks